United States Patent [19]

McShane et al.

[11] Patent Number: 5,115,672

[45] Date of Patent: May 26, 1992

[54] SYSTEM AND METHOD FOR VALVE MONITORING USING PIPE-MOUNTED ULTRASONIC TRANSDUCERS

[75] Inventors: James L. McShane, Churchill Boro; Nancy H. Ulerich, Monroeville, both of Pa.

[73] Assignee: Westinghouse Electric Corp., Pittsburgh, Pa.

[21] Appl. No.: 653,574

[22] Filed: Feb. 11, 1991

[51] Int. Cl.⁵ .......................... E03B 7/07; F16K 37/00
[52] U.S. Cl. ...................................... 73/596; 73/168; 73/119 A; 137/554; 367/99; 376/245; 376/252
[58] Field of Search ............................ 73/592, 597–602, 73/119 A, 168, 572, 596; 137/554; 367/99; 376/245, 252

[56] References Cited

U.S. PATENT DOCUMENTS

| | | | |
|---|---|---|---|
| 4,095,457 | 6/1978 | Koda et al. | 73/597 |
| 4,201,092 | 5/1980 | Dau | 376/252 |
| 4,678,621 | 7/1987 | Callaghan et al. | 376/245 |
| 4,694,693 | 9/1987 | Gerlowski | 73/168 |
| 4,821,769 | 4/1989 | Mills et al. | 73/592 |
| 4,920,802 | 5/1990 | McMullin et al. | 73/597 |
| 4,977,778 | 12/1990 | Nafziger et al. | 73/597 |

FOREIGN PATENT DOCUMENTS

| | | | |
|---|---|---|---|
| 1153114 | 8/1983 | Canada | 137/554 |
| 0068581 | 4/1983 | Japan | 137/554 |
| 0192235 | 9/1985 | Japan | 73/592 |

*Primary Examiner*—Hezron E. Williams
*Assistant Examiner*—Rose Finley

[57] ABSTRACT

A system and method for determining the condition of one or more parameters of a valve, e.g., particularly a check valve in a fluid carrying pipe, by monitoring fluid turbulence downstream of the valve. An ultrasonic transmitter-receiver transducer pair provides a signal modulated by the fluid turbulence, which signal is demodulated and processed to obtain a signature or other signal indicative of the valve condition. The processes signature signal may additionally be compared with a measure of flow rate determined just upstream from the valve. By operating the ultrasonic system at high frequency and using appropriate detecting circuitry, low frequency interference from mechanical shocks and vibrations is avoided, yielding a reliable detection of the flow turbulence caused by the valve.

6 Claims, 2 Drawing Sheets

SYSTEM AND METHOD FOR VALVE MONITORING USING PIPE-MOUNTED ULTRASONIC TRANSDUCERS

BACKGROUND OF THE INVENTION

This invention relates to ultrasonic monitoring systems and methods and, more particularly, ultrasonic systems mounted on pipes for monitoring valve conditions.

Non-intrusive online monitoring of valves, such as check valves, has acquired a great importance in many industrial applications. In the nuclear industry, check valves and other comparable valves, though simple in function, are critical to safe plant operation. In fact, such valves are subject to NRC-specified periodic inspections that, in the past, have usually required time-consuming and expensive partial disassembly. Although systems are available for monitoring motor-operated valves, there remains a need for a reliable system for monitoring check valves and the like which would avoid disassembly and consequent down time.

In the past, there have been a number of check valve diagnostic methods developed and marketed, but each is characterized by certain limitations and disadvantages. Ultrasonic systems have been proposed for directly monitoring valves, by using external transducers in the pulse-echo or through-transmission modes. However, in attempting to mount external transducers on valve parts, difficulty is encountered in obtaining desired acoustic paths and good acoustic coupling, because of the non-uniform makes and styles of valves and the consequent differing geometries and exterior surface finishes.

An acoustic technique, commonly referred to as Acoustic Emission (AE), has been used in many different monitoring applications. In this method, external transducers mounted on a valve and operating in a passive listening mode respond to acoustic energy in the metal which results from impacts and/or vibrations of valve parts. In other words, the transducer acts only in a listening, or receiving mode, to pick up acoustic signals generated by the valve. However, such transducers are sensitive to unwanted vibration and noise pick-up, and the resulting acoustic signals are difficult to interpret.

Another approach makes use of a permanent magnet installed on a moving valve part, with means for sensing the position of the moving magnet by an external magnetic sensor. This method is limited in that it requires modification of the valve to install a magnet, and may not be useful in many applications, e.g., those involving carbon steel valves. In yet another approach, x-rays have been used to show the position and possibly the condition of internal parts of valves. However, the x-ray approach involves large, expensive equipment, and also generates safety concerns.

There thus remains a very practical commercial need for an improved monitoring system and method, particularly for check valves in a nuclear power plant environment. Although this invention is illustrated by showing the swing-type of check valve, which is the most common, it is to be understood that other types of check valves and similar valves are within the scope of the invention.

SUMMARY OF THE INVENTION

It is an object of this invention to provide an improved, reliable system for monitoring one or more conditions of a check valve installed in a fluid-carrying pipe, and particularly a pipe in a nuclear power plant. It is a further object to provide an ultrasonic technique which operates at a high carrier frequency, so as to avoid masking or confusion with lower frequency vibration signals not indicative of valve condition or operation.

In accordance with the above objects, this invention provides a system and method for ultrasonic detection of valve condition by monitoring turbulence in the water or other fluid downstream from the valve element, which turbulence is indicative of the valve condition. The system uses ultrasonic transducers coupled to the exterior of the pipe, and in particular adjacent to the downstream side of the valve. In a preferred embodiment, a continuous wave ultrasonic beam is transmitted across the pipe between one or more pairs of transducers, the transmitted beam being modulated by turbulence in the fluid being carried through the pipe. The received turbulence-modulated signal is band pass filtered to reject low frequency vibrational components and high frequency noise, and demodulated to provide a waveform representative of the fluid turbulence caused by the valve. The demodulated signal is processed to develop a turbulence signature, which signature in turn is analyzed by comparison with one or more other reference signals. In specific further embodiments, the valve signature is related to generated values of upstream fluid flow, valve acoustic emission, pipe acoustic emission or valve position signals. A signal comparing turbulence downstream from the valve with turbulence upstream may also be obtained and utilized in the analysis circuitry.

DESCRIPTION OF THE PREFERRED EMBODIMENTS

Figure 1:
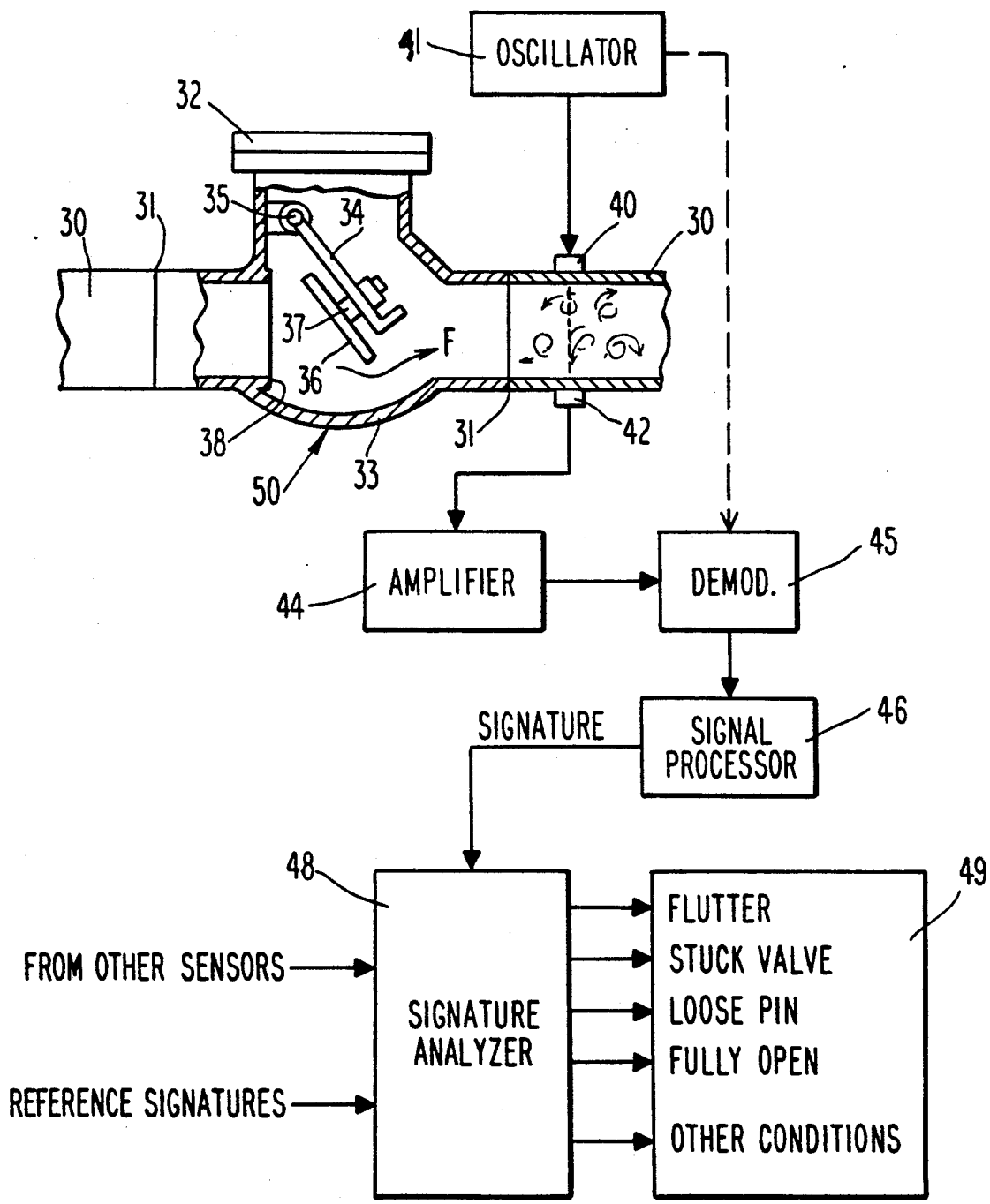
FIG. 1 is a simplified block diagram illustrating the system and method of this invention.

Referring first to FIG. 1, there is shown a valve 50 positioned in line with a pipe 30, the valve connections to the pipe being as illustrated by weld lines 31, although welded joints are not essential. The valve is illustrated as a check valve, but it is to be understood that other types of valves may be embraced within the scope of this invention. As illustrated, the valve has a top cover 32 and a valve body 33 containing the inside valve parts. Bolts (not shown) may be used to hold the cover in place. A rotating arm 34 is provided on a hinge pin 35, the arm swinging open in response to fluid flow from left to right, and swinging to a shut position in the event of reverse fluid flow. A disk 36 is connected to the arm 34 by a stud 37, the disk being dimensioned to seat against a seat 38 in a conventional manner when in the closed position. In practice, seat 38 should be at a slight angle to the vertical, for positive closing.

As illustrated, an ultrasonic transducer subsystem comprising transmit transducer 40 and receive transducer 42 is positioned just downstream of the valve. Although shown vertical in FIG. 1, the transducers and the acoustic path between them may have any rotational orientation, and more than one transducer pair can be used, with each pair oriented differently. A high frequency oscillator or signal generator 41 drives the transmit transducer, which typically is designed to operate at a high frequency in the range of 1-5 MHz, depending on the pipe size and material. As used herein, high frequency means at least an order of magnitude higher than the turbulence frequency, and preferably several orders of magnitude. In practice, the modulation frequencies caused by the downstream turbulence are typically less than 1 kHz. The output of receive transducer 42 is coupled into an amplifier 44 generally having a narrow band width centered on the ultrasonic carrier frequency. The narrow band width, which may be less than 10 kHz, encompasses the modulation spectrum but filters out lower frequencies which may be caused by mechanical vibration as well as high frequency noise from any source. The output of amplifier 44 is connected to a demodulator circuit 45, to derive a signal representative of the degree of modulation caused by the downstream turbulence. The demodulator may be an amplitude or phase demodulator, and in the latter case the reference signal from oscillator 41 is inputted to it, as indicated by the dashed line. The output of the demodulator circuit 45 is inputted to signal processor 46, which generates an output signature by any one of a number of standard techniques. For example, the signal processor may provide a frequency spectrum of the demodulated signal by means of a Fourier transform. The signature output is coupled to a signature analyzer 48, which compares the signature with signatures from other sources. Other sensors, including sensors positioned upstream, may generate signals which are processed to categorize and normalize the signature. Additional reference signatures may be generated in advance and stored in memory, and inputted into the signature analyzer for comparison. The comparison from the analyzer 48 results in an output which is indicative of one or more valve conditions such as flutter, a stuck valve, a loose pin, a fully open valve, etc. The indication may be provided by indication means 49, in the form of a video terminal output, a printed output, etc. Thus, the signal processor 46 identifies and quantizes significant characteristics of the turbulence waveform; the signature analyzer 48 relates these characteristics to valve status and condition.

Figure 2:
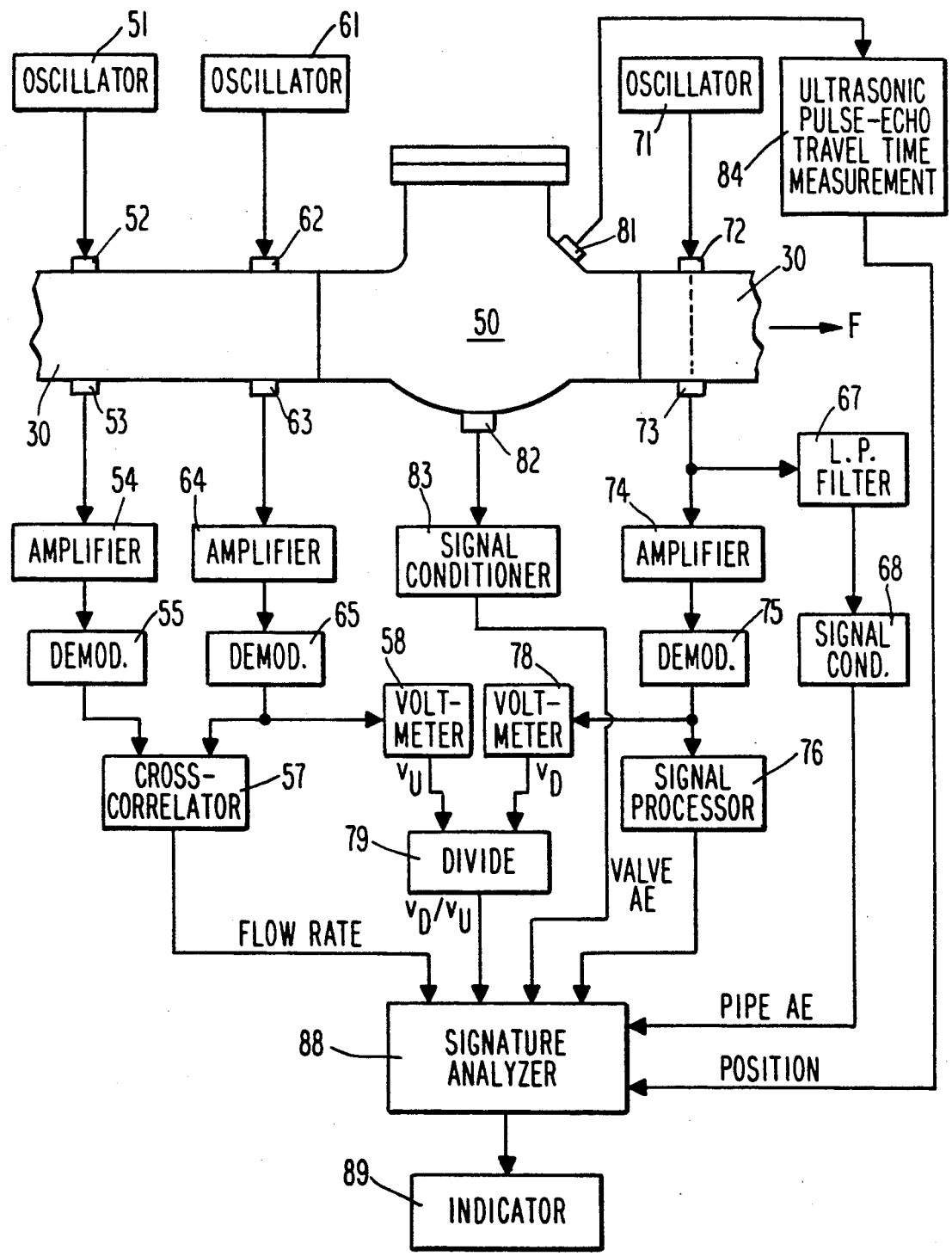
FIG. 2 is a more detailed block diagram illustrating additional embodiments of the system and method of this invention.

Referring now to FIG. 2, there is shown a more detailed block diagram, illustrating additional embodiments of the invention. As illustrated in FIG. 2, there are three ultrasonic subsystems, comprising elements 51-55, 61-65, and 71-75 respectively. Each subsystem is substantially similar, except for its positioning. The first two subsystems are positioned upstream from the valve 50, and provide demodulated signals which are connected into a cross-correlator circuit to determine an indication of flow rate. Such a flowmeter operates on the principle that the demodulated signals at the two respective positions along the pipe are cross-correlated to yield a fluid transit time between them, and hence velocity and flow rate. The transit time is taken to be the time delay between the two input waveforms for which the cross-correlation function is a maximum.

The third ultrasonic subsystem, comprising element 71-75, is arranged downstream from the valve in the same manner as elements 41-45 illustrated in FIG. 1. The output of demodulator 75 is processed through signal processor 76 and inputted to signature analyzer 88, the output of which is coupled to indicator 89. Additionally, the output of receive transducer 73 is connected to a low-pass filter 67, which passes primarily the lower frequency signals caused by mechanical vibration. The output of filter 67 is conditioned at signal conditioner circuit 68 to provide an output which is representative of pipe acoustic emission (AE). This pipe AE signal is inputted to signature analyzer 88 to provide a further signal useful in determining an accurate valve condition indication. Thus, the pipe AE can be, in effect, subtracted from the turbulence signal, to eliminate any unwanted pipe AE contribution to that signal. Because AE-generated waves propagate readily through metal structures, the pipe AE signals can indicate events, such as tapping, in the valve in the same manner as a valve-mounted AE transducer can. Thus, pipe AE sensing can replace or complement valve AE sensing.

The determined flow rate from cross-correlator 57 is inputted to the signature analyzer, and can be used to indicate whether changes in the downstream signals sensed by the downstream subsystem are the result of valve conditions or flow variations. Flow rate itself is a valuable output quantity, since it shows that the valve is open. While other ultrasonic flowmeters could be used, the cross-correlation method has the advantage of using functions and circuits already required for sensing and interpreting valve-induced turbulence. Also, sensing modulation upstream of the valve provides a reference to turbulence in a region which is undisturbed by the valve internals or conditions. In another embodiment not illustrated in the drawing, the signal from demodulation circuit 55 or 65 may be processed through a signal processor which matches circuit 76, and inputted to analyzer 88 as a reference signal.

To account for factors such as water temperature, temperature gradients, or bubbles, which can change the magnitude of signal modulation, a comparison of modulation magnitude, such as in terms of rms voltage, is made by using the two voltmeter circuits, 58, 78, which are coupled to the outputs of demodulator 65 and 75 respectively. The voltmeter outputs are connected to divide circuit 79, which provides an output representative of the downstream turbulence magnitude divided by the upstream turbulence magnitude, which is also inputted into the signature analyzer. Another input is provided by mounting an acoustic emission (AE) transducer 82 on the bottom side of the valve, as illustrated. This transducer provides an input representative of opening, closing and tapping impacts. The output of transducer 82 is processed at signal conditioner circuit 83, and inputted to the signature analyzer 88 as a signal representative of valve AE.

Yet another input to signature analyzer 88 is provided by having one or more ultrasonic transducers as illustrated at 81, which operate in the pulse-echo mode. Conventional circuitry, illustrated at 84, is used for driving transducer 81, processing detected return echo signals, and measuring the echo travel time. The echo travel time is representative of position, and may be indicative of missing valve parts. It is to be understood that a plurality of transducers as illustrated at 81 may be used at different locations to obtain such valve position and part information. The output signals from circuit 84 are likewise coupled into signature analyzer 88 for use in determining the valve condition. It should be noted that transducers such as 81 and 82 and associated electronics serve an auxiliary function for the primary pipe-mounted transducers and associated electronics.

An experimental flow loop was set up to test the invention of this application. A four-inch (about 10 cm) swing check valve was installed in the flow loop. Two pairs of 2.5 MHz transducers were held in diametrical alignment and spring loaded against the steel pipe surface, with a grease couplant used to provide acoustic coupling. Several positions of transducers were tried, specifically including an arrangement having one pair downstream and one pair upstream of the valve. With water flowing, time waveforms and frequency spectra were recorded and observed as the valve disk position was manually moved by the use of an external linkage provided for the tests. The flow rate was set to a value (about 100 gallons per minute, 13.4 cubic feet per minute) which caused the valve to be about 65% open. The demodulated signals from the downstream and upstream transducer pairs were recorded on a chart recorder as the valve disk assembly was manually forced partly closed against the flow, then rapidly opened. The disk position output voltage from a potentiometer driven by the mechanical linkage was also recorded, as was the DC output of an rms voltmeter reading the downstream demodulated signal. The results showed that the downstream signal and the resulting voltmeter reading from it increased significantly when the valve was more nearly closed, and decreased when the valve was fully opened. The voltmeter output waveform closely resembled the potentiometer output waveform as the disk assembly was repeatedly moved back and forth. On the other hand, the upstream signal changed very little because flow rate did not change much during manual operation of the valve. These results indicate that the downstream signal change is a good indication of increased turbulence following the valve when and as the flow is restricted perhaps by the disk stuck partly open. Further, the upstream signal is a good reference, as described above.

Occasionally, during tests, trapped air would become entrained. Its arrival at the valve caused large changes in both upstream and downstream signals, indicating that valve changes were not the cause of the downstream effect.

In another test, valve flutter was simulated by moving the disk assembly back and forth at about a 2.5 Hz rate. This action was detected as a large peak in the frequency spectrum of the downstream turbulence waveform at that frequency.

It is thus seen that the system and method of this invention provide a reliable means of monitoring the condition of a valve such as a check valve by obtaining information of the effects in the fluid flowing through the valve. This system provides freedom from unwanted sensitivity to mechanical shocks and vibrations, and provides the simplicity of mounting the transducers on the cylindrical pipe surface rather than on the complex-shaped valve body itself. Also, pipes are made in a limited number of standard sizes. While the invention has been described in terms of its preferred embodiments, it is to be understood that it is not limited to the details of those embodiments. For example, various types of signals can be used to drive the transmitting transducer, e.g., a modulated carrier rather than straight CW, or a series of pulses. There is no limit on the forms of modulation and demodulation used in at the practice of the invention, and indeed different types of modulation may be used with respect to the same valve to detect different conditions. Switching and multiplexing of various signals can, of course, be employed. With respect to the signature analyzing step, signature analysis techniques, e.g., artificial intelligence or expert systems, are well known in the art, and any such well known techniques may be employed in the practice of this invention. This signature analyzer may be a dedicated piece of electronic hardware, or may embody a computer with software adapted for the particular application. Further, in an environment such as a nuclear power plant where there are a large number of pipes to be monitored, the signals from each valve monitoring system may be coupled into a common computer with appropriate input/output hardware, for ongoing analysis.

The system may have the form of a portable instrument with easily installed transducers for use during inspections and servicing, or alternately may be permanently installed for continuous monitoring. Particularly for the latter case, dry coupling of transducers to the pipe, as in other systems made by the assignee, assures reliable long-term operation. If pulses are transmitted, rather than continuous signals, the turbulence effect can be sensed as pulse-to-pulse magnitude or travel time fluctuations.

We claim:

1. A method of monitoring a condition of a check valve in a fluid carrying pipe, by ultrasonic monitoring of turbulence in the fluid downstream from said valve, comprising:
   transmitting ultrasonic signals through said pipe and said fluid at a position adjacent to and downstream of said valve where said transmitted signal is modulated by the downstream turbulence of the fluid;
   receiving said transmitted signal and demodulating same to obtain a demodulated signal representative of said downstream turbulence; and
   processing said demodulation signal to obtain an indication of an operating condition of said valve.

2. The method as described in claim 1, wherein said processing step includes the step of determining a signature corresponding to said demodulated signal, and comparing said signature with at least one reference signal.

3. The method as described in claim 1, comprising determining flow rate of said fluid upstream of said valve, and comparing said processed signal with said flow rate.

4. The method as described in claim 1, comprising generating and transmitting through said fluid carrying pipe at a position upstream of said valve, an ultrasonic signal substantially equivalent to that of said signal transmitted downstream of said valve, demodulating said upstream signal, and comparing said upstream and downstream demodulated signals.

5. The method as described in claim 1, further comprising obtaining a sensed acoustic emission signal representative of valve acoustic emission, and comparing said process signal with said valve acoustic emission signal.

6. The method as described in claim 1, comprising obtaining an ultrasonic pulse-echo measure of the position of said valve, and wherein said analyzing step comprises analyzing said process signal together with said position signal to provide an indication of valve condition.

* * * * *